United States Patent
Bit

(10) Patent No.: US 7,135,588 B2
(45) Date of Patent: Nov. 14, 2006

(54) METHOD OF PRODUCING DIMETHYL PHTHALATE FROM NAPHTHALENE BASED CHEMICALS

(75) Inventor: Kumares Chandra Bit, Jharkhand (IN)

(73) Assignee: Council of Scientific and Industrial Research, New Delhi (IN)

( * ) Notice: Subject to any disclaimer, the term of this patent is extended or adjusted under 35 U.S.C. 154(b) by 426 days.

(21) Appl. No.: 10/793,700

(22) Filed: Mar. 5, 2004

(65) Prior Publication Data

US 2004/0215035 A1  Oct. 28, 2004

(30) Foreign Application Priority Data

Mar. 5, 2003  (IN) .......................... 213/Del/2003

(51) Int. Cl.
 *C07C 67/48* (2006.01)

(52) U.S. Cl. ....................................... 560/78

(58) Field of Classification Search ............... 560/78
See application file for complete search history.

(56) References Cited

OTHER PUBLICATIONS

Dubey et al., Reactions of Phthalic Anhydride with Alcohols, 1997, Asian Journal of Chemistry, vol. 9, No. 3, 1997, p. 379-387.*
Chemical Abstracts, vol. 43, Jul. 25, 1949, 5767a.

\* cited by examiner

*Primary Examiner*—Taylor Victor Oh
(74) *Attorney, Agent, or Firm*—Foley & Lardner LLP

(57) ABSTRACT

The present invention results to an improved and environment friendly method of producing dimethyl phthalate of about 99% purity from naphthalene based chemicals, said method comprising steps of mixing phthalic anhydride with methanol in the ratio ranging between 2:3 to 3:2, adding catalyst(s) to the mixture wherein, the ratio of phthalic anhydride and the catalyst is ranging between 3:1 to 15:1, adding a promoter to the resultant of step (b) wherein, the promoter is in the range of 1.5 to 2.0% by weight of phthalic anhydride, refluxing the resulted mixture at a temperature ranging between 60 to 100° C., for time duration ranging between 6 to 12 hrs. in the presence of benzene, wherein the ratio of benzene to phthalic anhydride is in the range of 1:5 to 2:1 to obtain distillate, neutralizing the residue with about 10% caustic soda, extracting the neutralized residue with the benzene, distilling at the temperature ranging between 140 to 150° C. under 10 mm of mercury to obtain dimethyl phthalate.

4 Claims, No Drawings

METHOD OF PRODUCING DIMETHYL PHTHALATE FROM NAPHTHALENE BASED CHEMICALS

FIELD OF THE PRESENT INVENTION

The present invention relates to a method of producing dimethyl phthalate. The present invention particularly relates to a method of producing dimethyl phthalate from naphthalene based chemicals, particularly, phthalic anhydride, which is a coal tar by product.

BACKGROUND AND PRIOR ART REFERENCES

Dimethyl phthalate is known to be an effective and safe repellent for blood sucking insects like mosquitoes and flies. It finds extensive application as a plasticizer, as a carrier in the dyeing of synthetic polyesters, as a froth flotation agent and an ingredient in hair sprays.

Generally, dimethylphthalate is obtained by direct oxidation of hydrocarbons. Reference may be made to "Chemical Abstract (CA) Vol. 43, (1949) 5767a". wherein phthalic anhydride and chloro sulphonic acid were refluxed. But very low yield was the drawback of the process.

Reference may be made to Ind. Engg. Chem 40,96 (1948) wherein oxides of aluminium, manganese and lead were used as catalyst. Low yield was the main drawback of the process.

Prior art search for producing dimethyl phthalate was made based on literature survey and patent data bases, which did not yield any relevant references.

OBJECTS OF THE PRESENT INVENTION

The main object of the present invention is to provide a method of producing dimethyl phthalate, having 98% purity, which obviates the drawbacks as detailed above.

Another object of the present invention is to provide a method of producing dimethyl phthalate from naphthalene based chemicals, particularly, phthalic anhydride, which is a coal tar by product.

Yet another object of the present invention is to provide a method of producing dimethyl phthalate which is environment friendly.

Still another object of the present invention is to provide a method of producing dimethyl phthalate which is economical.

SUMMARY OF THE PRESENT INVENTION

The present invention relates to a method of producing dimethyl phthalate. The present invention particularly relates to a method of producing dimethyl phthalate from naphthalene based chemicals, particularly, phthalic anhydride, which is a coal tar by product.

DETAILED DESCRIPTION OF THE PRESENT INVENTION

The present invention relates to an improved and environment friendly method of producing dimethyl phthalate of about 99% purity from naphthalene based chemicals, said method comprising steps of:

a) mixing phthalic anhydride with methanol in the ratio ranging between 2:3 to 3:2, b) adding catalyst(s) to the mixture wherein, the ratio of phthalic anhydride and the catalyst is ranging between 3:1 to 15:1, d) adding a promoter to the resultant of step (b) wherein, the promoter is in the range of 1.5 to 2.0% by weight of phthalic anhydride, e) refluxing the resulted mixture of step (d) at a temperature ranging between 60 to 100° C., for time duration ranging between 6 to 12 hrs. in the presence of benzene, wherein the ratio of benzene to phthalic anhydride is in the range of 1:5 to 2:1 to obtain distillate, f) separating the distillate into aqueous and benzene layers, g) recycling the benzene layer after removing the aqueous layer, h) recovering un-reacted methanol and residue from the layers by distillation, i) neutralizing the residue with about 10% caustic soda, j) extracting the neutralized residue with the benzene, k) distilling the extract under vacuum to obtain benzene, and l) continuing the distilling of step (k) at the temperature ranging between 140 to 150° C. under 10 mm of mercury to obtain dimethyl phthalate, m) optionally, dimethyl phthalate is further purified by decolorizing with activated charcoal.

Yet another object of the present invention, the phthalic anhydride is a coal tar by product.

Still another object of the present invention, the ratio of phthalic anhydride and catalyst is about 6:1.

Yet another object of the present invention, the catalyst is selected from a group comprising sulphuric acid and hydrochloric acid.

Still another object of the present invention, the ratio of catalysts is about 1:1.

Yet another object of the present invention, the promoter is dimethyl sulphate.

The invention provides a method of producing dimethyl phthalate from naphthalene based chemicals, particularly, phthalic anhydride, which is a coal tar by product. The phthalic anhydride is treated with methanol, in presence of a catalyst, such as sulphuric acid, hydrochloric acid or mixture thereof and a promoter, such as, dimethyl sulphate, and refluxing in presence of benzene. Processing to obtain dimethyl phthalate. Dimethyl phthalate is known to be an effective and safe repellent for blood sucking insects like mosquitoes. It finds extensive application as a plasticizer, as a carrier in the dyeing of synthetic polyesters, as a froth flotation agent and an ingredient in hair sprays.

The present invention provides a method of producing dimethyl phthalate from naphthalene based chemicals, particularly, phthalic anhydride, which is a coal tar by product, by treating phthalic anhydride with methanol, adding a catalyst, such as sulphuric acid, hydrochloric acid or mixture thereof and a promoter, such as, dimethyl sulphate. Refluxing the resultant mixture at a temperature in the range of 60 to 100 degree Celsius, for a time period in the range of 6 to 12 hours, in presence of benzene. Separating the distillate into two layers. Removing the aqueous layer and sending back the benzene layer to the reaction vessel. Recovering unreacted methanol by distillation. Neutralizing the residue with caustic soda followed by extraction with benzene. Distilling the extract under vacuum to obtain benzene, and continuing the distillation process at a temperature in the range of 145 to 146 degree Celsius under 10 mm of mercury to obtain dimethyl phthalate.

Accordingly the present invention provides a method of producing dimethyl phthalate, which comprises treating phthalic anhydride with methanol, adding a catalyst, such as sulphuric acid, hydrochloric acid or mixture thereof and a promoter, such as, dimethyl sulphate; refluxing the resultant mixture at a temperature in the range of 60 to 100 degree Celsius, for a time period in the range of 6 to 12 hours, in the presence of benzene; separating the distillate into two layers; removing the aqueous layer and recycling the benzene layer, recovering unreacted methanol by distillation; neutralizing the residue with caustic soda followed by extraction with benzene; distilling the extract under vacuum to obtain benzene; continuing the distillation process at a temperature in the range of 145 to 146 degree Celsius under 10 mm of mercury to obtain dimethyl phthalate.

In an embodiment of the present invention, the phthalic anhydride is a coal tar by product.

In another embodiment of the present invention, the ratio of phthalic anhydride and catalyst, is in the range of 3:1 to 15:1.

In yet another embodiment of the present invention, the ratio of phthalic anhydride and sulphuric acid, hydrochloric acid or mixture of equal amount of sulphuric acid and hydrochloric acid is in a ratio of 6:1.

In still another embodiment of the present invention, the promoter, dimethyl sulphate is in the range of 1.5 to 2.0% by weight of phthalic anhydride.

In still yet another embodiment of the present invention, the product can be further purified by declourising with activated charcoal.

In the present invention feed, phthalic anhydride, catalyst and promoter are heated for a time period within 6 to 12 hours in presence of benzene. The purpose of adding benzene is to remove water formed during the reaction as benzene water azeotrope. After completion of the reaction, unreacted methanol and benzene are recovered by distillation. The residue, containing the product and unconverted phthalic anhydride are neutralised with 10% caustic soda followed by extraction with benzene. The said extract is distilled under vacuum to obtain benzene and then the product of 98.5% purity is obtained within the temperature range of 145 to 146 degree Celsius. The product can be further purified by declourising with activated charcoal, if desired, as per IS 6627: 1972. The purity can be ascertained by Gas Chromatography and Infrared Spectroscopy.

The novelty of the present invention resides in producing dimethyl phthalate, useful as a potential insect repellant and a plasticizer, from naphthalene based chemicals, particularly, phthalic anhydride, which is a coal tar by product. The novelty of the present invention has been achieved by the inventive steps of treating phthalic anhydride with methanol, in the presence of a catalyst, such as sulphuric acid, hydrochloric acid or mixture thereof and a promoter, such as, dimethyl sulphate, refluxing in presence of benzene, followed by extraction to obtain enhanced yield of dimethyl phthalate.

The following examples are given by way of illustration of the present invention and should not be construed to limit the scope of the present invention.

EXAMPLES

Example-1

14.8 gms of phthalic anhydride, 24 gms by weight of methanol, 1 gm by weight of sulphuric acid and 3.5 gms by weight of hydrochloric acid and 0.25 gm by weight of dimethyl sulphate were taken in a three necked flask, made of glass, having provision for measuring reaction temperature, reflux condenser and arrangement for adding reactants to the reaction vessel. The resultant mixture was heated at 65 degree Celsius for 7 hours in presence of 4.4 gms by weight of benzene. The purpose of adding benzene was to remove water formed during the reaction as benzene water azeotrope. After completion of the reaction, unreacted methanol and benzene were recovered by distillation. The residue, containing the product and unconverted phthalic anhydride were neutralised with 10% caustic soda followed by extraction with benzene. The said extract was distilled under vacuum to obtain benzene and then 13.9 gms of product of 98.5% purity was obtained within the temperature range of 145 to 146 degree Celsius. Purity of the product was ascertained by Gas Chromatography and Infrared Spectroscopy.

Example-2

14.8 gms of phthalic anhydride, 24 gms by weight of methanol and 5.6 gms by weight of sulphuric acid and 0.25 gm by weight of dimethyl sulphate were taken in a three necked flask, made of glass, having provision for measuring reaction temperature, reflux condenser and arrangement for adding reactants to the reaction vessel. The resultant mixture was heated at 65 degree Celsius for 7 hours in presence of 18.0 gms by weight of benzene. The purpose of adding benzene was to remove water formed during the reaction as benzene water azeotrope. After completion of the reaction, unreacted methanol and benzene were recovered by distillation. The residue, containing the product and unconverted phthalic anhydride were neutralised with 10% caustic soda followed by extraction with benzene. The said extract was distilled under vacuum to obtain benzene and then 12.4 gms of product of 98.5% purity was obtained within the temperature range of 145 to 146 degree Celsius. Purity of the product was ascertained by Gas Chromatography and Infrared Spectroscopy.

Example-3

83 gms of phthalic anhydride, 75 gms by weight of methanol, 6.7 gm by weight of sulphuric acid and 1.6 gm by weight of dimethyl sulphate were taken in a three necked flask, made of glass, having provision for measuring reaction temperature, reflux condenser and arrangement for adding reactants to the reaction vessel. The resultant mixture was heated at 90 degree Celsius for 7 hours in presence of 18.0 gms by weight of benzene. The purpose of adding benzene was to remove water formed during the reaction as benzene water azeotrope. After completion of the reaction, unreacted methanol and benzene were recovered by distillation. The residue, containing the product and unconverted phthalic anhydride were neutralised with 10% caustic soda followed by extraction with benzene. The said extract was distilled under vacuum to obtain benzene and then 91 gms of product of 98.5% purity was obtained within the temperature range of 145 to 146 degree Celsius. Purity of the product was ascertained by Gas Chromatography and Infrared Spectroscopy.

In still another embodiment of the present invention, each step of the instant invention is critical to obtain the desired results. Further, the sequence of the steps is equally critical to obtain dimethyl phthalate of high purity. The Applicants have observed that any change in the sequence of the steps and manner of addition can lead to deleters effects on the out come of the reaction. The inventors have arrived at the instant invention after much experimental and trial.

The main advantages of the present invention are:
1. Producing dimethyl phthalate from naphthalene based chemicals, particularly, phthalic anhydride, which is a coal tar by product.
2. Product of high purity, of the order of 98%, can be achieved.
3. Economical method as cost of most of the materials is low.
4. No environmental pollution is involved in the process.

The invention claimed is:
1. A method of producing dimethyl phthalate comprising the steps of:
   a) mixing phthalic anhydride with methanol in the ratio ranging between 2:3 to 3:2,
   b) adding a catalyst to the mixture wherein, the ratio of phthalic anhydride and the catalyst is ranging between 3:1 to 15:1,
   c) adding a promoter to the resultant of step (b) wherein, the promoter is in the range of 1.5 to 2.0% by weight of phthalic anhydride,
   d) refluxing the resulted mixture of step (c) at a temperature ranging between 60 to 100° C., for time duration ranging between 6 to 12 hrs. in the presence of benzene, wherein the ratio of benzene to phthalic anhydride is in the range of 1:5 to 2:1 to obtain distillate,
   e) separating the distillate into aqueous and benzene layers,
   f) recycling the benzene layer after removing the aqueous layer,
   g) recovering un-reacted methanol and residue from the layers by distillation,
   h) neutralizing the residue with about 10% caustic soda,
   i) extracting the neutralized residue with the benzene,
   j) distilling the extract under vacuum to obtain benzene, and
   k) continuing the distilling of step (j) at the temperature ranging between 140 to 150° C. under 10 mm of mercury to obtain dimethyl phthalate,
   l) optionally purifying the dimethyl phthalate by decolorizing with activated charcoal wherein the catalyst is sulphuric acid or hydrochloric acid.

2. A method as claimed in claim 1, wherein the phthalic anhydride is a by-product of coal tar.

3. A method as claimed in claim 1, wherein the ratio of phthalic anhydride and catalyst is about 6:1.

4. A method as claimed in claim 1, wherein the promoter is dimethyl sulphate.

* * * * *